US012740929B2

(12) United States Patent
Oku et al.

(10) Patent No.: US 12,740,929 B2
(45) Date of Patent: Sep. 22, 2026

(54) OIL-IN-WATER EMULSION COSMETIC

(71) Applicant: SHISEIDO COMPANY, LTD., Tokyo (JP)

(72) Inventors: Rina Oku, Tokyo (JP); Ikuhiro Suzuki, Tokyo (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 227 days.

(21) Appl. No.: 18/705,975

(22) PCT Filed: Nov. 16, 2022

(86) PCT No.: PCT/JP2022/042498

§ 371 (c)(1),
(2) Date: Apr. 29, 2024

(87) PCT Pub. No.: WO2023/095691

PCT Pub. Date: Jun. 1, 2023

(65) Prior Publication Data

US 2025/0000768 A1 Jan. 2, 2025

(30) Foreign Application Priority Data

Nov. 29, 2021 (JP) ................................ 2021-193404

(51) Int. Cl.

| | |
|---|---|
| ***A61K 8/49*** | (2006.01) |
| ***A61K 8/06*** | (2006.01) |
| ***A61K 8/894*** | (2006.01) |
| ***A61Q 19/00*** | (2006.01) |

(52) U.S. Cl.

CPC ............ *A61K 8/4946* (2013.01); *A61K 8/894* (2013.01); *A61Q 19/00* (2013.01); *A61K 8/062* (2013.01); *A61K 2800/591* (2013.01)

(58) Field of Classification Search

None

See application file for complete search history.

(56) References Cited

U.S. PATENT DOCUMENTS

| | | | | |
|---|---|---|---|---|
| 2012/0183481 | A1 | 7/2012 | Iriyama et al. | |
| 2016/0220457 | A1* | 8/2016 | Yamaguchi .............. | A61Q 1/02 |
| 2023/0087483 | A1 | 3/2023 | Ueno et al. | |

FOREIGN PATENT DOCUMENTS

| | | | | | |
|---|---|---|---|---|---|
| JP | 2019-014709 | A | | 1/2019 | |
| JP | 2020-176085 | A | | 10/2020 | |
| JP | 2020180103 | A | * | 11/2020 | ............... A61K 8/29 |
| WO | WO-2011/040496 | A1 | | 4/2011 | |
| WO | WO-2021/177400 | A1 | | 9/2021 | |

OTHER PUBLICATIONS

Machine translation of Sasa (JP 2020-180103A) (2024).*

PCT International Preliminary Report on Patentability, dated Jun. 13, 2024, which includes a Translation of International Searching Authority, "Written Opinion," issued in connection with International Patent Application No. PCT/JP2022/042498, dated Dec. 20, 2022.

International Search Report dated Dec. 20, 2022 issued in International Patent Application No. PCT/JP2022/042498, with English translation, 5 pages.

* cited by examiner

*Primary Examiner* — H. Sarah Park

(74) *Attorney, Agent, or Firm* — Foley & Lardner LLP

(57) ABSTRACT

[Problem] To provide an oil-in-water emulsion cosmetic having an excellent feel in use.

[Solution] An oil-in-water emulsion cosmetic including (A) a cyclic carboxamide derivative having a specific structure or its salt, (B) polyoxyalkylene-modified silicone, (C) an oil, and (D) water.

6 Claims, No Drawings

OIL-IN-WATER EMULSION COSMETIC

CROSS-REFERENCE TO RELATED APPLICATIONS

This application claims priority under 37 U.S.C. § 371 to International Application No. PCT/JP2022/042988, filed on Nov. 16, 2022, which is based upon and claims priority of Japanese Patent Application No. 2021-0193404, filed on Nov. 29, 2021, the entire contents of all of which are incorporated herein by reference.

TECHNICAL FIELD

The present invention relates to an oil-in-water emulsion cosmetic.

BACKGROUND ART

An oil-in-water milk composition has been proposed in which polyoxyalkylene-modified silicone is contained and a silicone nanodisc is formed (Patent Literature 1). Such a composition has good emulsion stability, and enables an oil to be blended in an amount that cannot be achieved by normal solubilization, and a sticky feel can be suppressed. The users of such a composition have desired a more excellent feel in use, and there has been room for further improvement in the feel in use.

Meanwhile, a cyclic carboxamide derivative is known to have an anti-wrinkle effect and a pigmentation inhibitory effect, and is proposed to be blended in a cosmetic and the like (Patent Literature 2).

CITATION LIST

Patent Literature

Patent Literature 1: WO 2021/177400 A

Patent Literature 2: WO 2011/040496 A

SUMMARY OF THE INVENTION

According to the studies of the present inventors, it has been found that use of a cyclic carboxamide derivative in a cosmetic tends to cause a sticky feel. The present inventors have surprisingly found that an excellent feel in use can be achieved by using an oil-in-water cosmetic including a combination of polyoxyalkylene-modified silicone and a specific cyclic carboxamide derivative. The present invention is based on these findings.

According to the present invention, the following invention is provided.

[1] An oil-in-water emulsion cosmetic including:

(A) a cyclic carboxamide derivative or a salt of the cyclic carboxamide derivative, the cyclic carboxamide derivative represented by Formula (1):

[Chem. 1]

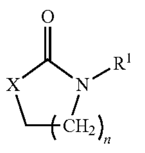

(1)

wherein $R^1$ represents a hydrocarbon group having 1 to 6 carbon atoms optionally substituted with a hydroxy group or $R^1$ represents a hydrogen atom, X represents $—CH_2—$ or $—N(R^2)—$ wherein $R^2$ represents a hydrocarbon group having 1 to 6 carbon atoms optionally substituted with a hydroxy group or $R^2$ represents a hydrogen atom, and n is an integer of 1 to 3;

(B) polyoxyalkylene-modified silicone;

(C) an oil; and (D) water.

[2] The cosmetic according to [1], wherein in Formula (1) of the component (A), $R^1$ represents a hydroxyalkyl group having 1 to 3 carbon atoms, X represents $—CH_2—$ or —NH—, and n is 1.

[3] The cosmetic according to [1] or [2], wherein the component (A) is 1-(2-hydroxyethyl)-2-imidazolidinone.

[4] The cosmetic according to any one of [1] to [3], wherein an amount of the component (A) blended is 0.05 to 7 mass % with respect to a total amount of the cosmetic.

[5] The cosmetic according to any one of [1] to [4], wherein the component (B) has a straight-chain silicone skeleton.

[6] The cosmetic according to any one of [1] to [5], wherein the component (B) has an HLB value of less than 10, the HLB value calculated with a Griffin method.

[7] The cosmetic according to any one of [1] to [6], wherein the component (B) is PEG-12 dimethicone.

[8] The cosmetic according to any one of [1] to [7], wherein an amount of the component (B) blended is 0.1 to 7 mass % with respect to the total amount of the cosmetic.

[9] The cosmetic according to any one of [1] to [8], wherein an amount of the component (C) blended is 0.5 to 30 mass % with respect to the total amount of the cosmetic.

[10] The cosmetic according to any one of [1] to [9], further including (E) a component selected from the group consisting of ethyl alcohol and dipropylene glycol.

[11] The cosmetic according to [10], wherein an amount of the component (E) blended is 1 to 20 mass % with respect to the total amount of the cosmetic.

According to the present invention, an oil-in-water emulsion cosmetic having an excellent feel in use can be provided. In particular, freshness is kept during application, a sticky feel is suppressed after application, and a moist feel can be further imparted to the skin.

BEST MODE FOR CARRYING OUT THE INVENTION

The present invention relates to an oil-in-water emulsion cosmetic (hereinafter, sometimes referred to as a cosmetic) including (A) a cyclic carboxamide derivative having a specific structure or its salt, (B) polyoxyalkylene-modified silicone, (C) an oil, and (D) water.

The cosmetic according to the present invention is a silicone nanodisc-containing cosmetic. It is considered that the silicone nanodisc containing no internal phase, which is formed by optimizing a vesicle to be a nanodisc precursor, is adsorbed to the oil droplet surface to maintain the emulsion stability.

(A) Cyclic Carboxamide Derivative or its Salt

The cosmetic according to the present invention includes a cyclic carboxamide derivative represented by Formula (1) or its salt (hereinafter, sometimes referred to as a component (A), and the same applies to other components).

[Chem. 2]

(1)

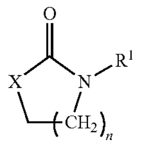

In Formula (1), $R^1$ represents a hydrocarbon group having 1 to 6 carbon atoms optionally substituted with a hydroxy group or $R^1$ represents a hydrogen atom, X represents-$CH_2$— or —$N(R^2)$— wherein $R^2$ represents a hydrocarbon group having 1 to 6 carbon atoms optionally substituted with a hydroxy group or $R^2$ represents a hydrogen atom, and n is an integer of 1 to 3

The hydrocarbon group is not particularly limited, and may be, for example, an alkyl group, a cycloalkyl group, an alkenyl group, an alkynyl group, a cycloalkylalkyl group, a haloalkyl group, an alkoxyalkyl group, or an alkoxycarbonylalkyl group, and is preferably an alkyl group.

In a preferred embodiment, in Formula (1) of the component (A), $R^1$ represents a hydroxyalkyl group having 1 to 3 carbon atoms, X represents —$CH_2$— or —NH—, and n is 1.

Specific examples of the cyclic carboxamide derivative represented by Formula (1) include the following.

[Chem. 3]

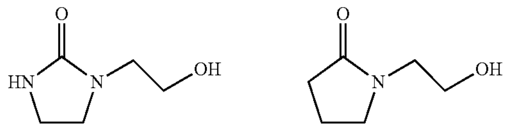

The component (A) is most preferably 1-(2-hydroxyethyl)-2-imidazolidinone.

The component (A) may be a salt of the cyclic carboxamide derivative represented by Formula (1). The kind of the salt is not particularly limited as long as the salt is pharmacologically acceptable, and the salt may be an inorganic salt or an organic salt. Examples of the inorganic salt include a hydrochloride, a sulfate, a phosphate, a hydrobromide, a sodium salt, a potassium salt, a magnesium salt, a calcium salt, a magnesium salt, and an ammonium salt. Examples of the organic salt include an acetate, a lactate, a maleate, a fumarate, a tartrate, a methanesulfonate, a p-toluenesulfonate, a triethanolamine salt, and an amino acid salt.

One or more kinds of the component (A) can be blended. The amount of the component (A) blended is preferably 0.05 to 7 mass %, more preferably 0.3 to 4 mass %, and still more preferably 0.5 to 3.5 mass % with respect to the total amount of the cosmetic.

(B) Polyoxyalkylene-Modified Silicone

The cosmetic according to the present invention includes (B) polyoxyalkylene-modified silicone. The component (B) has a linear or branched polysiloxane as a main skeleton and has a polyoxyalkylene group as a side chain. The component (B) preferably has a straight-chain silicone skeleton.

Examples of the polyoxyalkylene group include a polyoxyethylene group, a polyoxypropylene group, a polyoxybutylene group, a polyoxyethylene-polyoxypropylene group, and a polyoxyethylene-polyoxybutylene group, and a polyoxyethylene group is preferable. The polyoxyalkylene group preferably has an average polymerization degree of the monomer unit of 5 to 100 or less, more preferably 5 to 50, and still more preferably 10 to 15.

Examples of the substituent of the polysiloxane skeleton include hydrogen, alkyl groups having 1 to 6 carbon atoms, and aryl groups having 6 to 9 carbon atoms, and a methyl group is preferable.

The polysiloxane skeleton preferably has an average polymerization degree of the monomer unit of 3 to 550.

The component (B) preferably has an HLB value calculated with the Griffin method of less than 10, and more preferably 3 or more and less than 10.

A preferred embodiment of the component (B) is a component in which a part of the methyl groups of dimethicone is substituted with polyethylene glycol, and examples of the component include PEG-10 dimethicone and PEG-12 dimethicone, and PEG-12 dimethicone is preferable.

Examples of a commercially available product of PEG-12 dimethicone include DOWSIL ES-5373 (by Dow Toray Co, Ltd.), SH 3772 M, SH 3773 M, and SH 3775 M (all by Dow Corning Toray Silicone Co., Ltd.), and IM-22 (by Wacker Chemical Corporation).

One or more kinds of the component (B) can be blended. The amount of the component (B) blended is preferably 0.1 to 7 mass %, and more preferably 1 to 4 mass % with respect to the total amount of the cosmetic.

(C) Oil

The cosmetic according to the present invention includes (C) an oil. Examples of the component (C) include hydrocarbon oils, silicone oils (excluding the component (B)), ester oils, higher fatty acids, higher alcohols, liquid oils, solid oils, and semi-solid oils, and the component (C) is preferably selected from the group consisting of hydrocarbon oils, silicone oils, and ester oils.

Examples of the hydrocarbon oils include isododecane, isohexadecane, isoparaffin, mineral oil (liquid paraffin), ozokerite, squalane, pristane, paraffin, ceresin, squalene, petrolatum, microcrystalline wax, and hydrogenated polydecene.

Examples of the silicone oils include chain polysiloxanes (such as dimethicone, diphenylsiloxy phenyl trimethicone, and diphenylpolysiloxane), cyclic polysiloxanes (such as octamethylcyclotetrasiloxane, decamethylcyclopentasiloxane, and dodecamethylcyclohexasiloxane), silicone resins forming a three-dimensional network structure, silicone rubber, various modified polysiloxanes (such as an amino-modified polysiloxane, an alkyl-modified polysiloxane, and a fluorine-modified polysiloxane), and acrylic silicones, and chain polysiloxanes are preferable.

Examples of the ester oils include octyl octanoate, nonyl nonanoate, cetyl octanoate, isopropyl myristate, octyldodecyl myristate, isopropyl palmitate, ethylhexyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprate, tripropylene glycol pivalate, diisostearyl malate, glyceryl di-2-heptylundecanoate, glyceryl diisostearate, trimethylolpropane tri-2-ethylhexanoate, trimethylolpropane triisostearate, pentaerythritol tetra-2-ethylhexanoate, glyceryl tri-2-ethylhexanoate (triethylhexanoin), glyceryl trioctanoate, glyceryl triisopalmitate, trimethylolpropane triisostearate, cetyl 2-ethylhexanoate-2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, triethyl citrate, cetyl ethylhexanoate, and phytosteryl macadamiate.

Examples of the higher fatty acids include lauric acid, myristic acid, palmitic acid, stearic acid, behenic acid, oleic acid, undecylenic acid, tall oil acid, isostearic acid, linolic acid, linoleic acid, eicosapentaenoic acid (EPA), and docosahexaenoic acid (DHA).

Examples of the higher alcohols include straight-chain alcohols (such as lauryl alcohol, cetyl alcohol, stearyl alcohol, behenyl alcohol, myristyl alcohol, oleyl alcohol, and cetostearyl alcohol) and branched alcohols (such as lanolin alcohol, cholesterol, phytosterol, hexyldodecanol, isostearyl alcohol, and octyldodecanol).

Examples of the liquid oils include avocado oil, *camellia* oil, macadamia nut oil, corn oil, olive oil, rapeseed oil, sesame oil, persic oil, wheat germ oil, sasanqua oil, castor oil, linseed oil, safflower oil, cottonseed oil, *perilla* oil, soybean oil, peanut oil, tea seed oil, kaya oil, rice bran oil, *Paulownia* oil, Japanese tung oil, jojoba oil, germ oil, and triglycerin oil. Examples of the solid oils include cacao butter, coconut oil, hardened coconut oil, palm oil, palm kernel oil, hydrogenated palm oil, Japan wax kernel oil, hardened oils, Japan wax, and hardened castor oil. Examples of the semi-solid oils include shea butter, partially hydrogenated coconut oil, and partially hydrogenated jojoba oil.

One or more kinds of the component (C) can be blended. The amount of the component (C) blended is preferably 0.5 to 30 mass %, and more preferably 1 to 15 mass % with respect to the total amount of the cosmetic.

(D) Water

The cosmetic according to the present invention includes (D) water. As the water, water used in cosmetics, quasi-drugs, and the like can be used, and for example, purified water, ion-exchanged water, tap water, or the like can be used.

The amount of the water blended is preferably 20 to 95 mass %, and more preferably 60 to 90 mass % with respect to the total amount of the cosmetic according to the present invention.

(E) Component Selected from Group Consisting of Ethyl Alcohol and Dipropylene Glycol.

The cosmetic according to the present invention can further include (E) a component selected from the group consisting of ethyl alcohol (ethanol) and dipropylene glycol. The component (E) may include either ethyl alcohol or propylene glycol or include both of them, but preferably includes both ethyl alcohol and propylene glycol.

The amount of the component (E) blended is preferably 1 to 20 mass %, and more preferably 3 to 16 mass % with respect to the total amount of the cosmetic.

(F) Ionic Surfactant

The cosmetic according to the present invention can further include (F) an ionic surfactant. If the component (F) is further included, the stability is further improved. The component (F) is not particularly limited as long as it is different from the component (B) and is a surfactant exhibiting ionicity.

The component (F) is preferably an anionic surfactant, and more preferably a sulfonate anionic surfactant, and examples thereof include sulfosuccinic acid diester salts, alkyl aryl sulfonates, alkyl ether sulfonates, sulfosuccinic acid ester salts, acyl methyl taurine salts, and acyl taurine salts.

The component (F) is more preferably an N-acyl methyl taurine salt, and particularly preferably sodium methyl stearoyl taurate.

One or more kinds of the component (F) can be blended. The amount of the component (F) blended is preferably 0.001 to 0.5 mass %, and more preferably 0.005 to 0.1 mass % with respect to the total amount of the cosmetic.

(G) Thickener

The cosmetic according to the present invention can further include (G) a thickener. Examples of the component (G) include gum arabic, carrageenan, karaya gum, tragacanth gum, carob gum, quince seed (*Pyrus cydonia*), casein, dextrin, gelatin, sodium pectinate, sodium alginate, methylcellulose, ethylcellulose, CMC, hydroxyethylcellulose, hydroxypropylcellulose, PVA, PVM, PVP, sodium polyacrylate, a carboxyvinyl polymer (carbomer), a (dimethylacrylamide/sodium acryloyldimethyltaurate) crosspolymer, an (ammonium acryloyldimethyltaurate/VP) copolymer, an (ammonium acryloyldimethyltaurate beheneth-25 methacrylate) crosspolymer, a (sodium acrylate/sodium acryloyldimethyltaurate) copolymer, locust bean gum, guar gum, tamarind gum, dialkyldimethylammonium sulfate cellulose, xanthan gum, magnesium aluminum silicate, bentonite, hectorite, magnesium aluminum silicate (VEEGUM), laponite, and silicic anhydride.

One or more kinds of the component (G) can be blended. The amount of the component (G) blended is preferably 0.05 to 3 mass %, and more preferably 0.2 to 1 mass % with respect to the total amount of the cosmetic.

In the cosmetic according to the present invention, an optional component usually used in cosmetics and pharmaceuticals can be blended in addition to the above-described components. Examples of the optional component include the following components, and one or more kinds of them can be blended as long as an effect of the present invention is exhibited.

Examples of the moisturizer include polyethylene glycol, propylene glycol, glycerin, 1,3-butylene glycol (BG), erythritol, xylitol, sorbitol, maltitol, chondroitin sulfate, hyaluronic acid, mucoitinsulfuric acid, charonin acid, atelocollagen, cholesteryl-12-hydroxystearate, sodium lactate, bile acid salts, dl-pyrrolidone carboxylates, short-chain soluble collagen, a chestnut rose extract, a yarrow extract, and a melilot extract.

Examples of the metal ion sequestering agent include 1-hydroxyethane-1,1-diphosphonic acid, 1-hydroxyethane-1,1-diphosphonic acid tetrasodium salt, edetate disodium (EDTA-2Na), edetate trisodium, edetate tetrasodium, sodium citrate, sodium polyphosphate, sodium metaphosphate, gluconic acid, phosphoric acid, citric acid, succinic acid, edetic acid, and trisodium hydroxyethyl ethylenediamine triacetate.

Examples of the neutralizer include 2-amino-2-methyl-1-propanol, 2-amino-2-methyl-1,3-propanediol, potassium hydroxide, sodium hydroxide, triethanolamine, and sodium carbonate.

Examples of a pH adjuster include buffers such as lactic acid-sodium lactate, citric acid-sodium citrate, and succinic acid-sodium succinate.

Examples of the antioxidant include dibutylhydroxytoluene, butylhydroxyanisole, sodium pyrosulfite, and gallic acid esters.

Examples of the preservative include paraoxybenzoic acid esters such as methylparaben, ethylparaben, and butylparaben, benzoic acid, salicylic acid, sorbic acid, parachlorometacresol, hexachlorophene, benzalkonium chloride, chlorhexidine chloride, trichlorocarbanilide, photosensitizers, and phenoxyethanol.

Examples of the drug include ascorbic acid (vitamin C), tranexamic acid, kojic acid, ellagic acid, arbutin, alkoxysalicylic acid, glycyrrhizic acid, tocopherol, retinol, salts and derivatives thereof (for example, sodium L-ascorbate, L-ascorbic acid ester magnesium salt, L-ascorbic acid glucoside, 2-O-ethyl-L-ascorbic acid, 3-O-ethyl-L-ascorbic acid, 4-methoxysalicylic acid sodium salt, 4-methoxysalicylic acid potassium salt, dipotassium glycyrrhizinate, stearyl glycyrrhizinate, tocopherol acetate, retinol acetate, and retinol palmitate), nicotinic acid and its derivatives (for example, nicotinic acid amide), caffeine, tannin, verapamil and its derivatives, a licorice extract, glabridin, a hot water extract of Pyracantha fortuneana seed, various herbal medicines, hydrolyzed silk, hydrolyzed conchiolin, a tea extract, a *Potentilla erecta* root extract, an *Angelica keiskei* leaf/stem extract, an *Aloe barbadensis* leaf extract, a cherry leaf extract, an *Angelica acutiloba* Kitagawa root extract, a *Citrus depressa* peel extract, an *Iris florentina* root extract, an *Eucheuma serra/Grateloupia sparsa/Saccharina angustata/Ulva linza/Undaria pinnatifida* extract, a *Typha angustifolia* spike extract, an *Isodonis japonicus* leaf/stalk extract, a *Camellia japonica* seed extract, a *Saccharina angustata/Undaria pinnatifida* extract, a *Bupleurum falcatum* root extract, a *Nasturtium officinale* leaf/stem extract, a *Cinnamomum cassia* bark extract, a rosemary leaf oil, a lavender oil, glutamic acid, trimethylglycine, chlorphenesin, and methoxypropanediol.

In addition, an ultraviolet absorber, a powder component, an aroma chemical, and the like can also be appropriately blended.

The method for producing the cosmetic according to the present invention is not particularly limited, but, for example, the cosmetic can be produced with the following method.

An aqueous phase and (B) polyoxyethylene-modified silicone are mixed to form a vesicle as a precursor of a nanodisc. Here, the aqueous phase is not particularly limited as long as it is a formulation containing water and, if necessary, a component (E) as a main medium, and in addition to water or an aqueous solvent, a component usually used in cosmetics can be blended in an amount within a range in which the stability of the nanodisc is not impaired.

To the aqueous phase containing the vesicle as a precursor of a nanodisc, (C) an oil is added and stirred to transfer the vesicle as a precursor of a nanodisc to a nanodisc at an oil-water interface, and the nanodisc is adsorbed to form a highly stable cosmetic. Other components may be blended in the aqueous phase in advance before the vesicle formation, or may be blended after the vesicle formation.

Examples of the cosmetic according to the present invention include skin care cosmetics (such as lotions, milky lotions, creams, beauty essences, packs, and masks), makeup cosmetics (such as foundations and makeup bases), skin cleaning agents (such as face washes and makeup removers), sunscreen cosmetics, and ointments. These embodiments are merely examples, and the cosmetic according to the present invention is not limited to these embodiments.

EXAMPLES

The present invention will be described specifically with reference to the following Examples, but the present invention is not limited to these Examples. The content is shown in mass % with respect to the total amount unless otherwise specified.

Examples 1 to 12 and Comparative Examples 1 to 3

Cosmetics of Examples 1 to 12 and Comparative Examples 1 to 3 were prepared at combinations shown in Tables 1 and 2. The numerical values in the table are shown in mass %.

TABLE 1

| | Example | | | | | | | |
|---|---|---|---|---|---|---|---|---|
| | 1 | 2 | 3 | 4 | 5 | 6 | 7 | 8 |
| 1-(2-Hydroxyethyl)-2-imidazolidinone | 1.5 | 0.1 | 0.5 | 3 | 5 | 1.5 | 1.5 | 1.5 |
| PEG-12 dimethicone (HLB = 8) (*1) | 1 | 1 | 1 | 1 | 1 | 0.5 | 3 | 5 |
| Hydrogenated polydecene | 2 | 2 | 2 | 2 | 2 | 2 | 2 | 2 |
| Dimethicone | 1 | 1 | 1 | 1 | 1 | 1 | 1 | 1 |
| Triethylhexanoin | 1 | 1 | 1 | 1 | 1 | 1 | 1 | 1 |
| Water | Balance | Balance | Balance | Balance | Balance | Balance | Balance | Balance |
| Ethanol | 8 | 8 | 8 | 8 | 8 | 8 | 8 | 8 |
| Dipropylene glycol | 5 | 5 | 5 | 5 | 5 | 5 | 5 | 5 |
| Sodium methyl stearoyl taurate | 0.01 | 0.01 | 0.01 | 0.01 | 0.01 | 0.01 | 0.01 | 0.01 |
| Xanthan gum | 0.2 | 0.2 | 0.2 | 0.2 | 0.2 | 0.2 | 0.2 | 0.2 |
| Carbomer | 0.25 | 0.25 | 0.25 | 0.25 | 0.25 | 0.25 | 0.25 | 0.25 |
| Glycerin | 5 | 5 | 5 | 5 | 5 | 5 | 5 | 5 |
| Potassium hydroxide | 0.18 | 0.18 | 0.18 | 0.18 | 0.18 | 0.18 | 0.18 | 0.18 |
| Phenoxyethanol | 0.35 | 0.35 | 0.35 | 0.35 | 0.35 | 0.35 | 0.35 | 0.35 |

TABLE 1-continued

| | Example | | | | | | | |
|---|---|---|---|---|---|---|---|---|
| | 1 | 2 | 3 | 4 | 5 | 6 | 7 | 8 |
| EDTA-2Na | 0.1 | 0.1 | 0.1 | 0.1 | 0.1 | 0.1 | 0.1 | 0.1 |
| PEG-60 hydrogenated castor oil | — | — | — | — | — | — | — | — |
| Total | 100 | 100 | 100 | 100 | 100 | 100 | 100 | 100 |
| Stability | ○ | ○ | ○ | ○ | ○ | ○ | ○ | ○ |
| Freshness during application | A | A | A | A | A | A | A | B |
| Absence of sticky feel of skin after application | A | A | A | A | B | B | A | A |
| Moist feel of skin after application | A | B | A | A | A | A | A | A |

TABLE 2

| | Example | | | | Comparative Example | | |
|---|---|---|---|---|---|---|---|
| | 9 | 10 | 11 | 12 | 1 | 2 | 3 |
| 1-(2-Hydroxyethyl)-2-imidazolidinone | 1.5 | 1.5 | 1.5 | 1.5 | — | 1.5 | 1.5 |
| PEG-12 dimethicone (HLB = 8) (*1) | 1 | 1 | 1 | 1 | 1 | — | — |
| Hydrogenated polydecene | 5 | 2 | 2 | 2 | 2 | 2 | 2 |
| Dimethicone | 2.5 | 1 | 1 | 1 | 1 | 1 | 1 |
| Triethylhexanoin | 2.5 | 1 | 1 | 1 | 1 | 1 | 1 |
| Water | Balance | Balance | Balance | Balance | Balance | Balance | Balance |
| Ethanol | 8 | 8 | 8 | — | 8 | 8 | 8 |
| Dipropylene glycol | 5 | 5 | — | 5 | 5 | 5 | 5 |
| Sodium methyl stearoyl taurate | 0.01 | — | 0.01 | 0.01 | 0.01 | 0.01 | — |
| Xanthan gum | 0.2 | 0.2 | 0.2 | 0.2 | 0.2 | 0.2 | 0.2 |
| Carbomer | 0.25 | 0.25 | 0.25 | 0.25 | 0.25 | 0.25 | 0.25 |
| Glycerin | 5 | 5 | 5 | 5 | 5 | 5 | 5 |
| Potassium hydroxide | 0.18 | 0.18 | 0.18 | 0.18 | 0.18 | 0.18 | 0.18 |
| Phenoxyethanol | 0.35 | 0.35 | 0.35 | 0.35 | 0.35 | 0.35 | 0.35 |
| EDTA-2Na | 0.1 | 0.1 | 0.1 | 0.1 | 0.1 | 0.1 | 0.02 |
| PEG-60 hydrogenated castor oil | — | — | — | — | — | — | 0.5 |
| Total | 100 | 100 | 100 | 100 | 100 | 100 | 100 |
| Stability | ○ | ○ | ○ | ○ | ○ | X | ○ |
| Freshness during application | A | A | A | A | A | — | C |
| Absence of sticky feel of skin after application | A | A | A | A | A | — | C |
| Moist feel of skin after application | A | A | A | A | D | — | A |

(*1) DOWSIL ES-5373 (by Dow Toray Co, Ltd.)

The cosmetic prepared above was observed visually and with an optical microscope immediately after preparation, and the stability was evaluated in accordance with the following criteria. The obtained results are as shown in Tables 1 and 2.

○: Separation of an oil is not visually confirmed, and remarkable coalescence and enlargement of emulsified particles are not confirmed with an optical microscope.

x: Separation of an oil is visually confirmed, and remarkable coalescence and enlargement of emulsified particles are confirmed with an optical microscope.

The cosmetic prepared above was applied to the skin of seven expert panelists, and the panelists evaluated "freshness during application", "absence of a sticky feel of the skin after application", and the "moist feel of the skin after application". Determination was made in accordance with the following criteria on the basis of the evaluation of each expert panelist. The obtained results are as shown in Tables 1 and 2.

[Freshness During Application]

A: Five or more of the seven panelists answered that a fresh feel was present.

B: Three or more and four or less of the seven panelists answered that a fresh feel was present.

C: One or more and two or less of the seven panelists answered that a fresh feel was present.

D: All of the seven panelists answered that a fresh feel was absent.

[Absence of Sticky Feel of Skin after Application]

A: Five or more of the seven panelists answered that a sticky feel was absent.

B: Three or more and four or less of the seven panelists answered that a sticky feel was absent.

C: One or more and two or less of the seven panelists answered that a sticky feel was absent.

D: All of the seven panelists answered that a sticky feel was present.

[Moist Feel of Skin after Application]

A: Five or more of the seven panelists answered that a moist feel of the skin was present.

B: Three or more and four or less of the seven panelists answered that a moist feel of the skin was present.

C: One or more and two or less of the seven panelists answered that a moist feel of the skin was present.

D: All of the seven panelists answered that a moist feel of the skin was absent.

The invention claimed is:

1. An oil-in-water emulsion cosmetic comprising:

(A) 1-(2-hydroxyethyl)-2-imidazolidinone, an amount of the component (A) blended is 0.5 to 3.5 mass % with respect to a total amount of the cosmetic;

(B) PEG-10 dimethicone or PEG-12 dimethicone, an amount of the component (B) blended is 1 to 4 mass % with respect to the total amount of the cosmetic;

(C) an oil; and (D) water.

2. The cosmetic according to claim 1, wherein the component (B) is PEG-10 dimethicone.

3. The cosmetic according to claim 1, wherein the component (B) is PEG-12 dimethicone.

4. The cosmetic according to claim 1, wherein an amount of the component (C) blended is 0.5 to 30 mass % with respect to the total amount of the cosmetic.

5. The cosmetic according to claim 1, further comprising (E) a component selected from the group consisting of ethyl alcohol and dipropylene glycol.

6. The cosmetic according to claim 5, wherein an amount of the component (E) blended is 1 to 20 mass % with respect to the total amount of the cosmetic.

* * * * *